US005925748A

United States Patent [19]
Stone et al.

[11] Patent Number: 5,925,748
[45] Date of Patent: Jul. 20, 1999

[54] DNA DIAGNOSTICS FOR GLAUCOMA

[75] Inventors: Edwin M. Stone, Iowa City; Val C. Sheffield, Coralville; Wallace L.M. Alward, Iowa City, all of Iowa

[73] Assignee: The University of Iowa Research Foundation, Iowa City, Iowa

[21] Appl. No.: 08/748,479

[22] Filed: Nov. 8, 1996

Related U.S. Application Data

[63] Continuation-in-part of application No. 08/234,218, Apr. 28, 1994.
[51] Int. Cl.$^6$ .......................... C07H 21/02; C07H 21/04; C07H 19/00; C07H 21/00
[52] U.S. Cl. .................... 536/23.1; 536/24.31; 536/23.5; 435/6; 435/91.2
[58] Field of Search .................... 435/6, 91.2; 536/23.1, 536/23.5, 24.31

[56] References Cited

U.S. PATENT DOCUMENTS

5,606,043  2/1997  Nguyen et al. ........................ 536/23.5

FOREIGN PATENT DOCUMENTS

WO 96/14411  5/1996  WIPO ............................ C12N 15/12
WO 96/33287  10/1996  WIPO ............................ C12Q 1/68

OTHER PUBLICATIONS

Escribano, J. et al. (1995) "Isolation and Characterization of Cell–Specific cDNA Clones from a Substractive Library of the Ocular Ciliary Body of a Single Normal Human Donor: Transcription and Synthesis of Plasma Proteins", *J. Biochem.*, 118:921–931.

Ortega, J. et al. (1997), "Cloning and Characterization of Subtracted cDNAs from a Human Ciliary Body Library Encoding TIGR, a Protein Involved in Juvenile Open Angle Glaucoma with Homology to Myosin and Olfactomedin", *FEBS Letters*, 413:349–353.

Stone, Edwin M. et al. (1997) "Identification of a Gene that Causes Primary Open Angle Glaucoma", *Science*, 275:668–670.

Sunden, Sara L.F. et al. (1996) "Fine Mapping of the Autosomal Dominant Juvenile Open Angle Glaucoma (GLC1A) Region and Evaluation of Candidate Genes" *Genome Res.*, 6:862–869; and International Search Report (PCT/US97/20702) Mar. 13, 1998.

"CHLC Report" (Newsletter), Cooperative Human Linkage Center, vol. 1, pp. 1–18, May 1993.

"Editorial: Genetic Associations of Glaucoma", *British Journal of Ophthalmology*, vol. 64, pp. 225–226, 1980.

Cotton, P., "Glaucoma Gene Mapped to Chromosome 1", *JAMA*, vol. 269, No. 21, p. 2715, Jun. 2, 1993.

Francois, J., "Genetics and Primary Open–Angle Glaucoma", *Am. J. Ophthalmol.*, vol. 61, pp. 652–665, 1966.

Harris, D., "The Inheritance of Glaucoma: A Pedigree of Familial Glaucoma", *Am. J. Ophthalmol.*, vol. 60, pp. 91–95, 1965.

Johnson, A.T. et al., "Clinical Features and Linkage Analysis of a Family with Autosomal Dominant Juvenile Glaucoma", *Ophthalmology*, vol. 100, No. 4, pp. 524–528, Apr. 1993.

Kolker, A.E., "Glaucoma Family Study: Ten–Year Follow–up (Preliminary Report)", *Israel J. Med. Sci.*, vol. 8, No. 8–9, pp. 1357–1361, Aug.–Sep. 1972.

Leighton, D.A., "Survey of the First–degree Relatives of Glaucoma Patients", *Trans. Ophthal. Soc. U.K.* vol. 96, pp. 28–32, 1976.

Martin, J.P. and E.C. Zorab, "Familial Glaucoma in Nine Generations of a South Hampshire Family", *Brit. J. Ophthal.*, pp. 536–542, 1974.

Miller, S.J.H. and G.D. Paterson, "Studies on Glaucoma Relatives", *Brit. J. Ophthalmol.*, vol. 46, pp. 513–522, 1962.

Orita, M. et al., "Detection of Polymorphisms of Human DNA by Gel Electrophoresis as Single–Strand Conformation Polymorphisms", *Proc. Natl. Acad. Sci. USA,* vol. 86, pp. 2766–2770, Apr. 1989.

Perkins, E.S., "Family Studies in Glaucoma", *Brit. J. Ophthal.*, vol. 58, pp. 529–535, 1974.

Richards, J.E. et al., "Mapping of a Gene for Autosomal Dominant Juvenile–Onset Open–Angle Glaucoma to Chromosome Iq", *Am. J. Hum. Genet.*, vol. 54, pp. 62–70, 1994.

Sheffield, V.C., et al., "Attachment of a 40–Base–Pair G+C–Rich Sequence (GC–clamp) to Genomic DNA Fragments by the Polymerase Chain Reaction Results in Improved Detection to Single–Base Changes", *Proc. Natl. Acad. Sci. USA,* vol. 86, pp. 232–236, Jan. 1989.

Sheffield, V.C., et al., "Genetic Linkage of Familial Open Angle Glaucoma to Chromosome 1q21–q31", *Nature Genetics*, vol. 4, pp. 47–50, May 1993.

Weatherill, J.R. and Hart, C.T., "Familial Hypoplasia of the Iris Stroma Associated with Glaucoma" *Brit. J. Ophthal.,* vol. 53, pp. 433–438, 1969.

*Primary Examiner*—Deborah Crouch
*Assistant Examiner*—Jill D. Martin
*Attorney, Agent, or Firm*—Foley, Hoag & Eliot LLP; Beth E. Arnold; Anita Varma

[57] ABSTRACT

Methods and kits for diagnosing a subject with glaucoma or with a predisposition for developing glaucoma are disclosed.

10 Claims, 5 Drawing Sheets

GAA CTC GAA CAA ACC TGG GAG ACA AAC ATC

CGT AAG CAG TCA GTC GCC AAT GCC TTC ATC

ATC TGT GGC ACC TTG TAC ACC GTC AGC AGC
                                              CAC(TYR430HIS)

TAC ACC TCA GCA GAT GCT ACC GTC AAC TTT

GCT TAT GAC ACA GGC ACA GGT ATC AGC AAG

ACC CTG ACC ATC CCA TTC AAG AAC.CGC TAT

AAG TAC AGC AGC ATG

Fig. 4A

ATA CTG CCT AGG CCA CTG GAA AGC ACG GGT

CGT GTG GTG TAC TCG GGG AGC CTC TAT TTC

CAG GGC GCT GAG TCC AGA ACT GTC ATA AGA

TAT GAG CTG AAT ACC GAG ACA GTG AAG GCT
TAC(TYR340TYR)           AAG(GLU345LYS)

GAG AAG GAA ATC CCT GGA GCT GGC TAC CAC
                                                      GTC(GLY357VAL)

GGA CAG TTC CCG TAT TCT TGG GGT GGC TAC
    TAG(GLN361STOP)

ACG GAC ATT G

Fig. 4B

PREVALENCE OF GCL1A GENE MUTATIONS IN FOUR POPULATIONS

|  | Familial Glaucoma[1] (n=247) | Unselected Glaucoma[2] (n=95) | General Population[3] (n=358) | Normal Volunteers[4] (n=91) |
|---|---|---|---|---|
| TYR340TYR | 21(8.5%) | 3(3.2%) | 9(2.5%) | 2(2.2%) |
| GLU345LYS | 1(0.04%) | 0(0%) | 0(0%) | 0(0%) |
| GLY357VAL | 2(0.03%) | 0(0%) | 0(0%) | 0(0%) |
| GLN361STOP | 6(2.4%) | 2(2.1%) | 1(0.28%) | 0(0%) |
| TYR430HIS | 1(0.04%) | 0(0%) | 0(0%) | 0(0%) |

1 Unrelated probands with at least one living first degree relative with glaucoma
2 Unrelated, consecutive patients seen in the UIHC glaucoma clinic
3 Unrelated patients with retinal disease (n= xx) and unrelated spouses from previous linkage studies (n=51)—these patients were collected without regard to personal or family history of glaucoma and were used as an approximation of the general population
4 Unrelated volunteers 40 years of age or older who do not have a personal or family history of glaucoma abd whose intraocular pressures were less than 20 mm Hg.

Fig. 5

SEQUENCE LISTING (1) GENERAL INFORMATION:

(iii) NUMBER OF SEQUENCES: 8

(2) INFORMATION FOR SEQ ID NO:1:

(i) SEQUENCE CHARACTERISTICS:
      (A) LENGTH: 20 base pairs
      (B) TYPE: nucleic acid
      (C) STRANDEDNESS: single
      (D) TOPOLOGY: linear (ii) MOLECULE TYPE: other nucleic acid
      (A) DESCRIPTION: /desc = "primer"

(xi) SEQUENCE DESCRIPTION: SEQ ID NO:1:

ATACTGCCTA GGCCACTGGA                                                              20

(2) INFORMATION FOR SEQ ID NO:2:

(i) SEQUENCE CHARACTERISTICS:
      (A) LENGTH: 19 base pairs
      (B) TYPE: nucleic acid
      (C) STRANDEDNESS: single
      (D) TOPOLOGY: linear (ii) MOLECULE TYPE: other nucleic acid
      (A) DESCRIPTION: /desc = "primer"

(xi) SEQUENCE DESCRIPTION: SEQ ID NO:2:

```
                  CAATGTCCGT GTAGCCACC                                                19

(2) INFORMATION FOR SEQ ID NO:3:

(i) SEQUENCE CHARACTERISTICS:
             (A) LENGTH: 20 base pairs
             (B) TYPE: nucleic acid
             (C) STRANDEDNESS: single
             (D) TOPOLOGY: linear (ii) MOLECULE TYPE: other nucleic acid
             (A) DESCRIPTION: /desc = "primer"

(xi) SEQUENCE DESCRIPTION: SEQ ID NO:3:

GAACTCGAAC AAACCTGGGA                                                20

(2) INFORMATION FOR SEQ ID NO:4:

(i) SEQUENCE CHARACTERISTICS:
             (A) LENGTH: 22 base pairs
             (B) TYPE: nucleic acid
             (C) STRANDEDNESS: single
             (D) TOPOLOGY: linear (ii) MOLECULE TYPE: other nucleic acid
             (A) DESCRIPTION: /desc = "primer"

(xi) SEQUENCE DESCRIPTION: SEQ ID NO:4:

CATGCTGCTG TACTTATAGC GG                                             22

(2) INFORMATION FOR SEQ ID NO:5:

(i) SEQUENCE CHARACTERISTICS:
             (A) LENGTH: 195 base pairs
             (B) TYPE: nucleic acid
             (C) STRANDEDNESS: single
             (D) TOPOLOGY: linear (ii) MOLECULE TYPE: DNA (genomic)

(xi) SEQUENCE DESCRIPTION: SEQ ID NO:5:

GAACTCGAAC AAACCTGGGA GACAAACATC CGTAAGCAGT CAGTCGCCAA TGCCTTCATC     60

ATCTGTGGCA CCTTGTACAC CGTCAGCAGC TACACCTCAG CAGATGCTAC CGTCAACTTT    120

GCTTATGACA CAGGCACAGG TATCAGCAAG ACCCTGACCA TCCCATTCAA GAACCGCTAT    180

AAGTACAGCA GCATG                                                    195

(2) INFORMATION FOR SEQ ID NO:6:

(i) SEQUENCE CHARACTERISTICS:
             (A) LENGTH: 195 base pairs
             (B) TYPE: nucleic acid
             (C) STRANDEDNESS: single
             (D) TOPOLOGY: linear (ii) MOLECULE TYPE: DNA (genomic)

(xi) SEQUENCE DESCRIPTION: SEQ ID NO:6:

GAACTCGAAC AAACCTGGGA GACAAACATC CGTAAGCAGT CAGTCGCCAA TGCCTTCATC     60

ATCTGTGGCA CCTTGCACAC CGTCAGCAGC TACACCTCAG CAGATGCTAC CGTCAACTTT    120

GCTTATGACA CAGGCACAGG TATCAGCAAG ACCCTGACCA TCCCATTCAA GAACCGCTAT    180

AAGTACAGCA GCATG                                                    195

(2) INFORMATION FOR SEQ ID NO:7:

(i) SEQUENCE CHARACTERISTICS:
```

-continued (A) LENGTH: 190 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:7:

ATACTGCCTA GGCCACTGGA AAGCACGGGT CGTGTGGTGT ACTCGGGGAG CCTCTATTTC     60

CAGGGCGCTG AGTCCAGAAC TGTCATAAGA TATGAGCTGA ATACCGAGAC AGTGAAGGCT    120

GAGAAGGAAA TCCCTGGAGC TGGCTACCAC GGACAGTTCC CGTATTCTTG GGGTGGCTAC    180

ACGGACATTG                                                          190

(2) INFORMATION FOR SEQ ID NO:8:

(i) SEQUENCE CHARACTERISTICS:
        (A) LENGTH: 190 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:8:

ATACTGCCTA GGCCACTGGA AAGCACGGGT CGTGTGGTGT ACTCGGGGAG CCTCTATTTC     60

CAGGGCGCTG AGTCCAGAAC TGTCATAAGA TACGAGCTGA ATACCAAGAC AGTGAAGGCT    120

GAGAAGGAAA TCCCTGGAGC TGTCTACCAC GGATAGTTCC CGTATTCTTG GGGTGGCTAC    180

ACGGACATTG                                                          190

DNA DIAGNOSTICS FOR GLAUCOMA

This application is a continuation-in-part of application Ser. No. 08/234,218, filed Apr. 28, 1994.

1. GOVERNMENT SUPPORT

Work described herein has been supported, in part, by Public Health Service Research Grants EY08426, P50HG00835 and HG00457. The U.S. Government may therefore have certain rights in the invention.

2. BACKGROUND OF THE INVENTION

Glaucoma is a diverse group of disorders characterized by a damaged optic nerve with resultant loss of peripheral vision and ultimately loss of central vision. In most cases, an elevated intraocular pressure is felt to play a role in the visual loss. Glaucoma is the second leading cause of permanent blindness in the United States and the single leading cause of blindness among African-Americans (Leske, M. C. (1983) *American Journal of Epidemiology* 118:166–191; Francois, J. (1966) *Am J. Ophthalmol* 61:652–665; Hoskins, H. D. et al. (1989) *Sixth ed. St. Louis: C. V. Mosby*) Glaucoma developing between birth and age three is termed primary infantile glaucoma. The majority of cases of glaucoma develop in adulthood after age forty. Juvenile glaucoma occurs later than infantile glaucoma but earlier than the usual adult forms (Hoskins, H. D. et al (1989) *Sixth ed. St. Louis: C. V. Mosby*).

Infantile glaucoma is thought to be caused by incomplete development of the anterior segment of the eye. In contrast, there are no developmental anomalies associated with the more prevalent adult forms of glaucoma. Children with infantile glaucoma typically have symptoms of tearing, photophobia, corneal clouding and large eyes by the time they reach one year of age.

Juvenile open angle glaucoma occurs after age three (when the eye ceases to grow in response to increased intra-ocular pressure) but before age forty. There are two forms of juvenile glaucoma; one that appears as a late form of infantile glaucoma with similar iridocorneal angle anomalies, and another that has normal angles and is similar to adult primary open angle glaucoma.

The adult onset glaucomas are subdivided by the mechanisms of pressure elevation into closed angle and open angle glaucoma. If the trabecular meshwork (located in the angle between the iris and cornea) is free from mechanical obstruction, the glaucoma is termed primary open angle glaucoma (POAG). Adult primary open angle glaucoma accounts for about 60–70% of all cases of glaucoma (Hoskins, H. D. et al (1989) *Sixth ed. St. Louis: C. V. Mosby*). Population surveys suggest that the prevalence of primary open angle glaucoma in the general population is between 0.63% and 1.25% (Banks, J. L. K. et al. (1968) *British Medical Journal* 1:791; Popovic, V. (1982) *Acta Ophthalmologica* 60:745–758). In these patients, there is an insidious increase in intra-ocular pressure, usually beginning late in life. The anterior segment of the eye appears normal by examination and there is no identifiable cause of the increased pressure. When damage to the optic nerve or loss of visual field is detected, the patient is diagnosed as having glaucoma. In some forms of adult primary open angle glaucoma with iris hypoplasia (Weatherill, J. R. et al (1969) *Br J Ophthalmol* 53:433–8; Berg, F. (1932) *Acta Ophthalmol* 10:568–587; Francois, J. et al (1950) *Bull Soc Belge Ophthal* 96:665–683; Hambresin, M. L. et al (1946) *Societe Francaise d'Ophthalmologie* 59:219–223; McCulloch, C. et al (1950) *Transcripts of the Canadian Ophthalmologic Society* 79–91).

It has been reported that 4–16% of first degree relatives of patients with POAG develop the disease (Phelps, C. D. & Podos, S. M., Glaucoma: In Genetic and Metabolic Eye Diseases (ed. Goldberg, M. F.) 237–259 (Little Brown, Boston, 1974); Miller, S. J. H. & Paterson, G. D., *Br. J Ophthalmol* 46, 513–522 (1962); and Leighton, D. A., *Trans. Ophthalmol. Soc. U.K.* 96: 28–32 (1976)) and that 13–47% of POAG patients have a positive family history (Phelps, C. D. & Podos, S. M., Glaucoma: In Genetic and Metabolic Eye Diseases (ed. Goldberg, M. F.) 237–259 (Little Brown, Boston, 1974); and Francois, J. *Am. J. Ophthalmol.* 61, 652–665 (1966)). In addition, there have been reports of the existence of families with clearly heritable open angle glaucoma (Harris, D. *Am. J Ophthalmol.* 60: 91–95 (1965); Francois, J. *Am. J. Ophthalmol.* 61:652–665 (1966); Waardenbeurg, P. J. *Genetica* 25: 79–129 (1950), Biro, I *Ophthalmologica* 122:228–238 (1951) and Johnson, A. T. et al., *Ophthalmology* 100: 524–529 (1993)).

Although these findings raise the possibility that a significant portion of glaucoma may be genetically determined, prior to the instant invention, a glaucoma causing gene had not been identified.

3. SUMMARY OF THE INVENTION

In one aspect, the invention features methods and kits for diagnosing a subject with glaucoma or with a predisposition for developing glaucoma. In a preferred embodiment, the diagnostic methods and kits utilize a set of primers for amplifying regions of the subjects genomic DNA or a complement thereof, which potentially contains a glaucoma causing mutation (i.e. a mutation in the gene causing juvenile onset primary open angle glaucoma (GLC1A), and a means for analyzing the amplification product for differences (mutations) from the normal coding sequence.

The instant disclosed diagnostic methods allow an ophthamologist to determine whether a presymptomatic individual at risk for developing glaucoma (based on family history) will develop the disease. If the diagnosis is negative, the individual will not have the worry of anticipating development of the disease over time. If the diagnosis is positive, steps may be taken to prevent or ameliorate the effects of the disease before damage, such as loss of vision, occurs.

Other features and advantages will be readily apparent from the following detailed description and claims.

4. BRIEF DESCRIPTION OF THE DRAWINGS

FIGS. 4A and 4B show the five amino-acid-altering sequence changes in the GLC1A gene that correlate to a predisposition to developing glaucoma.

FIG. 5 is a chart showing the prevalence of GCL1A Gene Mutations in Four Populations.

5. DETAILED DESCRIPTION OF THE INVENTION

5.1 General

Figure 1:
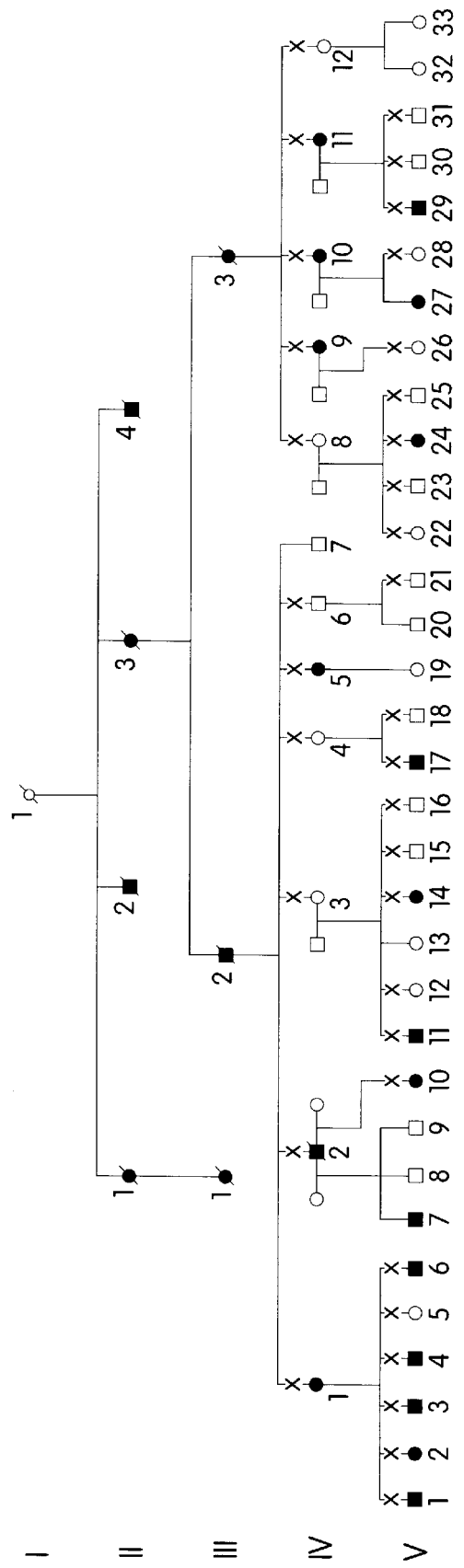
FIG. 1 shows the pedigree of the glaucoma family used in determining linkage of a glaucoma gene to chromosome 1q21-31.

The instant invention is based on linkage studies that have mapped a glaucoma causing gene to a region of human chromosome 1. As described in detail in the attached Example 1, linkage has been determined based on studies performed on a family with an autosomal dominant form of juvenile open angle glaucoma. The pedigree of this family is shown in FIG. 1. Of the thirty seven family members, nineteen were found to be affected based on findings of elevated intra-ocular pressure, optic nerve cupping and visual field loss. Three additional patients were considered to be affected on the basis of mildly elevated intra-ocular pressures and an obviously affected offspring. This family was used for linkage analysis with short tandem repeat polymorphisms (STRPs) (Weber, J. L. and P. E. May (1989) *Am. J Hum. Genet* 44:388–396; Litt, M. and J. A. Luty (1989) *Am. J. Hum. Genet.* 44:397–401; Weber, J. L. (1990) *Genomics* 7:524–530). The STRPs used were distributed across the entire genome. The family members were genotyped with over 90 STRPs before linkage was detected with markers that map to chromosome 1q. A total of 33 chromosome 1 markers were typed in this family and significant linkage to eight STRPs was demonstrated. The glaucoma locus was initially mapped to a 20 centimorgan (cM) region flanked by markers D1S191 and LAMB2 located in the region of 1q21–q31. Pairwise linkage analysis using marker D1S212 resulted in a lod score of 6.5 ($\theta$=0). Since this marker was fully informative in the family, multipoint analysis with other linked markers did not add to the peak lod score obtained with marker D1S212.

Figure 2:
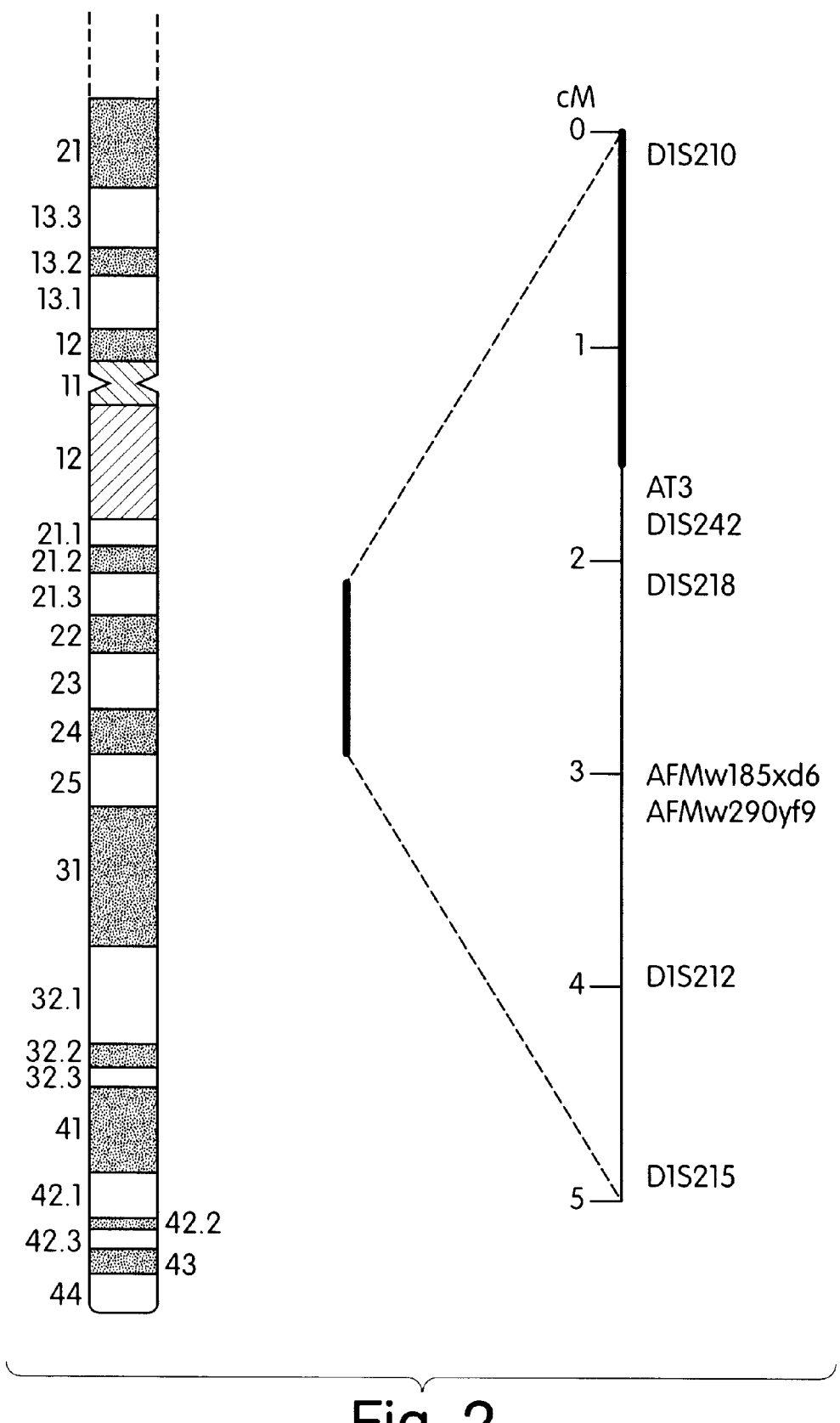
FIG. 2 is a map of human chromosome 1q showing relative positions of markers linked to a glaucoma causing gene.

A second large branch of the original family and two independent large juvenile glaucoma families were subsequently identified. Chromosome 1q linkage has been demonstrated in all three families. The additional meioses in the original family and one of the new families were used to narrow the candidate interval to an approximate 2.5 cM interval between markers D1S210 and AT3 as shown in FIG. 2. Primary linkage data has confirmed linkage at 1q in a large Michigan pedigree. All classic juvenile primary open angle glaucoma pedigrees tested to date (including a French-Canadian pedigree) appear to map to this locus, indicating that this locus is a major juvenile primary open angle glaucoma locus.

Figure 3:
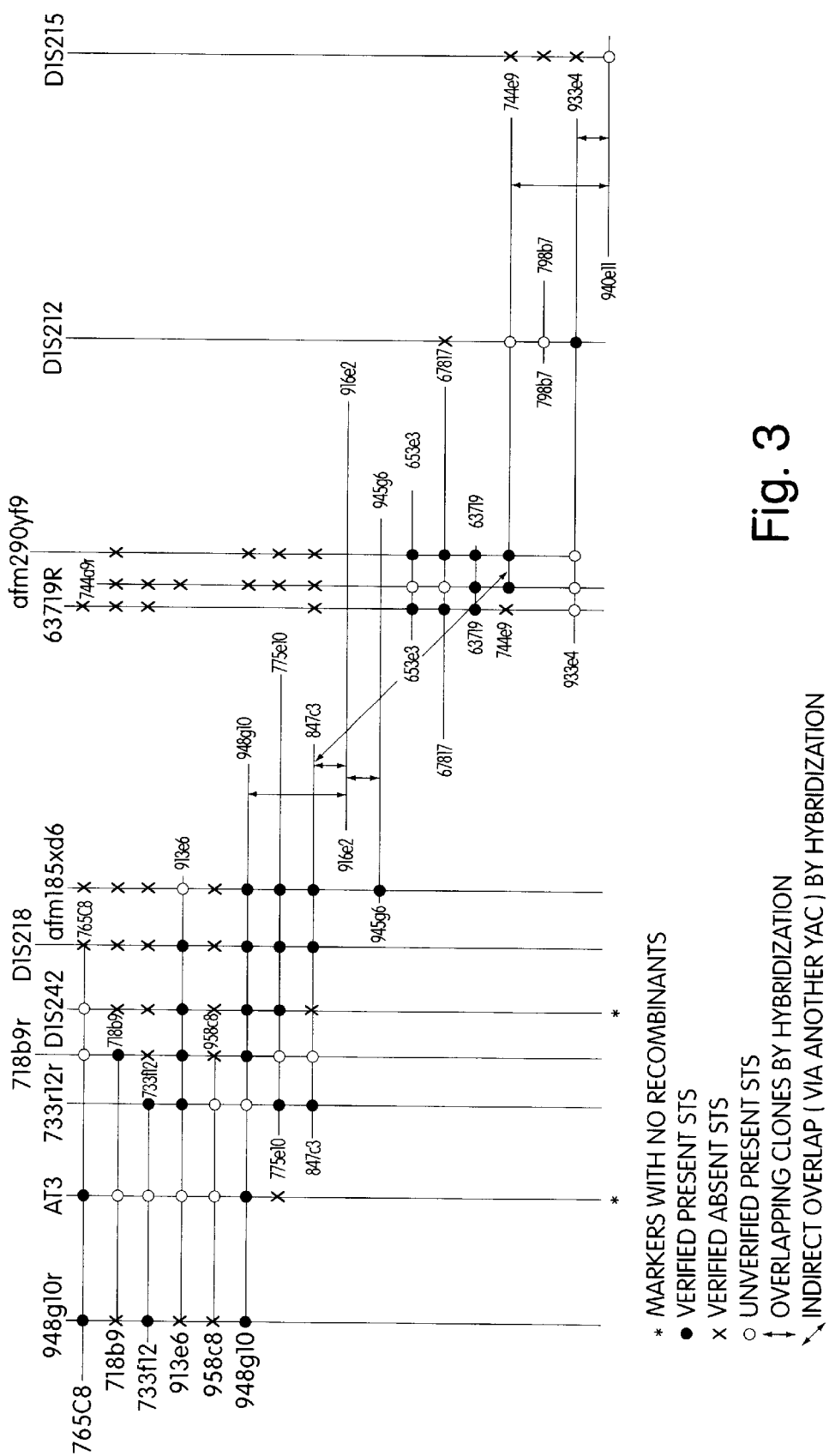
FIG. 3 is a graphic representation of a Yeast Artificial Chromosome (YAC) contig of the 1q glaucoma region.

In addition to genetic mapping, CEPH YAC and mega YAC libraries have been screened with the flanking markers and markers that show no recombination with the disease. Further, a YAC contig across the candidate interval has been generated and is shown in FIG. 3.

Diagnostic and Prognostic Assays

As described in the following Example 3, two primer pairs have been identified, which are capable of detecting the predisposition to glaucoma in the majority of glaucoma patients. These primers, which hybridize to a portion of the trabecular meshwork induced glucocorticoid response (TIGR) gene (International Publication No. WO 96/1441 to Nguyen et al.,) indicate that mutations in the TIGR gene, which maps within the interval of human chromosome 1 described herein, is causative of primary open angle glaucoma.

Identification of these primers makes testing for primary open angle glaucoma (POAG), which has been estimated to account for at least 60–70% of all cases of glaucoma, a reality. Diagnostic testing can now be performed on presymptomatic individuals, who are at risk of developing glaucoma based on family history. In addition, tests can be performed on postsymptomatic individuals diagnosed with glaucoma based on an ophthamologic examination. Further a diagnostic test could be performed on DNA obtained from a fetus in utero, although glaucoma would not appear to be a sufficiently life threatening or diabling disease to warrant prenatal identification.

Examples of appropriate biological samples for use in the instant invention include: solid materials (e.g tissue, cell pellets, biopsies) and biological fluids (e.g. urine, blood, saliva, amniotic fluid, mouth wash). Fetal nucleic acid samples can be obtained from maternal blood as described in International Patent Application No. WO91/07660 to Bianchi; alternatively amniocytes or chorionic villi may be obtained for performing prenatal testing.

Nucleic acid molecules (e.g. genomic DNA or complements thereof (e.g. mRNA) can be isolated from a particular biological sample using any of a number of procedures, which are well-known in the art, the particular isolation procedure chosen being appropriate for the particular biological sample. For example, freeze-thaw and alkaline lysis procedures can be useful for obtaining nucleic acid molecules from solid materials; heat and alkaline lysis procedures can be useful for obtaining nucleic acid molecules from urine; and proteinase K extraction can be used to obtain nucleic acid from blood (Rolff, A et al. PCR: Clinical Diagnostics and Research, Springer (1994)).

Diagnostic procedures may also be performed in situ directly upon tissue sections (fixed and/or frozen) of patient tissue obtained from biopsies or resections, such that no nucleic acid purification is necessary (e.g., Nuovo, G. J., 1992, PCR in situ hybridization: protocols and applications, Raven Press, NY).

It may be useful or essential to first amplify the complement of nucleic acid present in a sample prior to analysis using one of many possible means. Examples of appropriate amplification procedures for use in the invention include: cloning (Sambrook et al., Molecular Cloning: A Laboratory Manual, Cold Spring Harbor Laboratory Press, 1989), polymerase chain reaction (PCR) or RACE PCR (C. R. Newton and A. Graham, PCR, BIOS Publishers, 1994; U.S. Pat. Nos. 4,683,195 and 4,683,202, Saiki R. et al., (1988) *Science* 239:487–49), Q-Beta Replicase (Lizardi, P. M. et al., 1988, Bio/Technology 6:1197), ligase chain reaction (LCR) (Wiedmann, M., et. al., (1994) *PCR Methods Appl.* Vol. 3, Pp. 57–64; F. Barany *Proc. Natl. Acad. Sci USA* 88, 189–93 (1991), strand displacement amplification (SDA) (G. Terrance Walker et al., *Nucleic Acids Res.* 22, 2670–77 (1994)) and variations such as RT-PCR (Higuchi, et al., *Bio/Technology* 11:1026–1030 (1993)), allele-specific amplification (ASA), self sustained sequence replication (Guatelli, J. C. et al., 1990, Proc. Natl. Acad. Sci. USA 87:1874–1878) and transcription based processes (Kwoh, D. Y. et al., 1989, Proc. Natl. Acad. Sci. USA 86:1173–1177) or any other nucleic acid amplification method.

A preferred method for amplifying the nucleic acid present in the sample is PCR amplification using the instant disclosed primers, which specifically hybridize to portions of the human trabecular meshwork induced glucocorticoid (TIGR) gene resulting in amplification of a 190 base pair sequence that contains the majority of POAG mutations.

In a merely illustrative embodiment, the method includes the steps of (i) collecting a biological sample from a patient, (ii) isolating nucleic acid (e.g., genomic DNA, mRNA or both) from the sample, (iii) contacting the nucleic acid sample with one or more primers, which result in an amplification product comprised of a portion of the glaucoma gene potentially containing disease-causing mutations, and (iv) analyzing the amplification product to determine the presence of a glaucoma causing mutation.

The amplification product can be analyzed using any of a number of techniques, which are known to one of skill in the art. For example, any of a variety of sequencing reactions known in the art can be used to directly sequence the amplification product and detect mutations by comparing the sequence of the sample amplification product with the corresponding wild-type (control) sequence. Exemplary sequencing reactions include those based on techniques developed by Maxim and Gilbert (*Proc. Natl Acad Sci USA* (1977) 74:560) or Sanger (Sanger et al (1977) *Proc. Nat Acad. Sci* 74:5463). It is also contemplated that any of a variety of automated sequencing procedures may be utilized when performing the subject assays (*Biotechniques* (1995) 19:448), including sequencing by mass spectrometry (see, for example U.S. Pat. No. 5,547,835; WO94/21822 and WO 96/29431 by H. Köster). It will be evident to one skilled in the art that, for certain embodiments, the occurence of only one, two or three of the nucleic acid bases need be determined in the sequencing reaction. For instance, A-tract or the like, e.g., where only one nucleic acid is detected, can be carried out.

In a further embodiment, protection from cleavage agents (such as a nuclease, hydroxylamine or osmium tetroxide and with piperidine) can be used to detect mismatched bases in RNA/RNA or RNA/DNA heteroduplexes (Myers, et al. (1985) *Science* 230:1242). In general, the art technique of "mismatch cleavage" starts by providing heteroduplexes of formed by hybridizing (labelled) RNA or DNA containing the wild-type rp sequence with potentially mutant RNA or DNA obtained from a tissue sample. The double-stranded duplexes are treated with an agent which cleaves single-stranded regions of the duplex such as which will exist due to basepair mismatches between the control and sample strands. For instance, RNA/DNA duplexes can be treated with RNase and DNA/DNA hybrids treated with S1 nuclease to enzymatically digesting the mismatched regions. In other embodiments, either DNA/DNA or RNA/DNA duplexes can be treated with hydroxylamine or osmium tetroxide and with piperidine in order to digest mismatched regions. After digestion of the mismatched regions, the resulting material is then separated by size on denaturing polyacrylamide gels to determine the site of mutation. See, for example, Cotton et al (1988) *Proc. Natl Acad Sci USA* 85:4397; Saleeba et al (1992) Methods Enzymod. 217:286–295. In a preferred embodiment, the control DNA or RNA can be labeled for detection.

In still another embodiment, the mismatch cleavage reaction employs one or more proteins that recognize mismatched base pairs in double-stranded DNA (so called "DNA mismatch repair" enzymes) in defined systems for detecting and mapping point mutations in cDNAs obtained from samples of cells. For example, the mutY enzyme of *E. coli* cleaves A at G/A mismatches and the thymidine DNA glycosylase from HeLa cells cleaves T at G/T mismatches (Hsu et al. (1994) *Carcinogenesis* 15:1657–1662). According to an exemplary embodiment, a probe is hybridized to a cDNA or other DNA product from a test cell(s). The duplex is treated with a DNA mismatch repair enzyme, and the cleavage products, if any, can be detected from electrophoresis protocols or the like. See, for example, U.S. Pat. No. 5,459,039.

In other embodiments, alterations in electrophoretic mobility will be used to identify mutations. For example, single strand conformation polymorphism (SSCP) may be used to detect differences in electrophoretic mobility between mutant and wild type nucleic acids (Orita et al. (1989) *Proc Natl. Acad. Sci USA* 86:2766, see also Cotton (1993) *Mutat Res* 285:125–144; and Hayashi (1992) *Genet Anal Tech Appl* 9:73–79). Single-stranded DNA fragments of sample and control nucleic acids will be denatured and allowed to renature. The secondary structure of single-stranded nucleic acids varies according to sequence, the resulting alteration in electrophoretic mobility enables the detection of even a single base change. The DNA fragments may be labelled or detected with labelled probes. The sensitivity of the assay may be enhanced by using RNA (rather than DNA), in which the secondary structure is more sensitive to a change in sequence. In a preferred embodiment, the subject method utilizes heteroduplex analysis to separate double stranded heteroduplex molecules on the basis of changes in electrophoretic mobility (Keen et al. (1991) *Trends Genet* 7:5).

In yet another embodiment the movement of mutant or wild-type fragments in polyacrylamide gels containing a gradient of denaturant is assayed using denaturing gradient gel electrophoresis (DGGE) (Myers et al (1985) *Nature* 313:495). When DGGE is used as the method of analysis, DNA will be modified to insure that it does not completely denature, for example by adding a GC clamp of approximately 40 bp of high-melting GC-rich DNA by PCR. In a further embodiment, a temperature gradient is used in place of a denaturing agent gradient to identify differences in the mobility of control and sample DNA (Rosenbaum and Reissner (1987) *Biophys Chem* 265:12753).

Examples of other techniques for detecting point mutations include, but are not limited to, selective oligonucleotide hybridization, selective amplification, or selective primer extension. For example, oligonucleotide primers may be prepared in which the known mutation is placed centrally and then hybridized to target DNA under conditions which permit hybridization only if a perfect match is found (Saiki et al. (1986) *Nature* 324:163); Saiki et al (1989) *Proc. Natl Acad. Sci USA* 86:6230). Such allele speicific oligonucleotide hybridization techniques may be used to test one mutation per reaction when oligonucleotides are hybridized to PCR amplified target DNA or a number of different mutations when the oligonucleotides are attached to the hybridizing membrane and hybridized with labelled target DNA.

Alternatively, allele specific amplification technology which depends on selective PCR amplification may be used in conjunction with the instant invention. Oligonucleotides used as primers for specific amplification may carry the mutation of interest in the center of the molecule (so that amplification depends on differential hybridization) (Gibbs et al (1989) *Nucleic Acids Res.* 17:2437–2448) or at the extreme 3' end of one primer where, under appropriate conditions, mismatch can prevent, or reduce polymerase extension (Prossner (1993) *Tibtech* 11:238. In addition it may be desirable to introduce a novel restriction site in the region of the mutation to create cleavage-based detection (Gasparini et al (1992) *Mol. Cell Probes* 6:1). It is anticipated that in certain embodiments amplification may also be performed using Taq ligase for amplification (Barany (1991) *Proc. Natl. Acad. Sci USA* 88:189). In such cases, ligation will occur only if there is a perfect match at the 3' end of the 5' sequence making it possible to detect the presence of a known mutation at a specific site by looking for the presence or absence of amplification.

For mutations that produce premature termination of protein translation, the protein truncation test (PTT) offers an efficient diagnostic approach (Roest, et. al., (1993) *Hum. Mol. Genet.* 2:1719–21; van der Luijt, et. al., (1994) *Genomics* 20:1–4). For PTT, RNA is initially isolated from available tissue and reverse-transcribed, and the segment of interest is amplified by PCR. The products of reverse transcription PCR are then used as a template for nested PCR amplification with a primer that contains an RNA polymerase promoter and a sequence for initiating eukaryotic translation. After amplification of the region of interest, the unique motifs incorporated into the primer permit sequential in vitro transcription and translation of the PCR products. Upon sodium dodecyl sulfate-polyacrylamide gel electrophoresis of translation products, the appearance of truncated polypeptides signals the presence of a mutation that causes premature termination of translation. In a variation of this technique, DNA (as opposed to RNA) is used as a PCR template when the target region of interest is derived from a single exon.

The methods described herein may be performed, for example, by utilizing pre-packaged diagnostic kits comprising at least one primer pair, which may be conveniently used, e.g., in clinical settings to diagnose patients exhibiting symptoms or family history of glaucoma.

In addition to methods which focus primarily on the detection of one nucleic acid sequence, profiles may also be assessed in such detection schemes. Fingerprint profiles may be generated, for example, by utilizing a differential display procedure, Northern analysis and/or RT-PCR.

In another aspect, the invention features kits for use in diagnosing glaucoma or a predisposition to developing glaucoma. For instance, in one embodiment, the kit can comprise primers for amplifying regions of the subjects genomic DNA or a complement thereof, which potentially contains a glaucoma causing mutation. The kit can also comprise a means for analyzing the amplification product for differences (mutations) from the normal coding sequence and/or instructions for use.

The present invention is further illustrated by the following examples which should not be construed as limiting in any way. The contents of all cited references (including literature references, issued patents, published patent applications, and copending patent applications) cited throughout this application are hereby expressly incorporated by reference.

EXAMPLE 1

Genetic Linkage of Familial Open Angle Glaucoma to Chromosome 1q21-q31

Materials and Methods

Pedigree

A family in which five consecutive generations have been affected with juvenile-onset, open-angle glaucoma without iridocorneal angle abnormalities was identified. The family comprised descendants of a woman who emigrated from Germany to the midwestern United States in the late 1800s. The disease state in affected family members included onset during the first 3 decades of life, normal anterior chamber angles, high intraocular pressures, lack of systemic or other ocular abnormalities, and need for surgery to control the glaucoma in affected individuals. A total of 35 family members at 50% risk for glaucoma had complete eye examinations including visual acuity with refraction, slit-lamp biomicroscopy, applanation tomometry, gonioscopy, stereo disc photography and Humphrey, Goldmann or Octopus perimetry. Two other affected patients were ascertained by reviewing records of other opthalmologists. Patients were considered to be affected for linkage if they had documented pressures greater than 30 mm Hg and evidence of optic nerve or visual field damage; or, if they had intraocular pressures greater than 22 mm Hg and an obviously affected child. Affected family members are characterized by an early age of diagnosis, a normal appearing trabecular meshwork, very high intraocular pressures (often above 50 mm Hg), and relatively pressure-resistant optic nerves. FIG. 1 is a pictorial representation of the pedigree.

DNA typing

Blood samples were obtained from all living affected family members as well as six spouses of affected patients with children. 10 ml blood were obtained from each patient in EDTA-containing glass tubes. DNA was prepared from the blood using a nonorganic extraction procedure (Grimberg, J. et al. Nucl. Acids Res 17, 8390 (1989)). Short tandem repeat polymorphisms (STRPs) distributed across the entire autosomal genome were selected from the literature or from those kindly provided by J. L. Weber. The majority were [dC-dA]-[dG-dT] dinucleotide repeats. Oligonucleotide primers flanking each STRP were synthesized using standard phosphoramidite chemistry (Applied Biosystems model 391 DNA synthesizer). Amplification of each STRP was performed with 50 ng. of each patient's DNA in a 8.35 $\mu$l PCR containing each of the following: 1.25 $\mu$l 10 X buffer (100 mM Tris-HCl pH 8.8, 500 mM KCl, 15 mM $MgCl_2$, 0.01% w/v gelatin), 300 $\mu$M each of dCTP, dGTP and dTTP, 37 $\mu$M dATP, 50 pmoles each primer, 0.25 $\mu$l $\alpha$-$^{35}$S-dATP (Amersham,>1000 Ci $mmol^{-1}$), and 0.25 U Taq polymerase (Perkin-Elmer/Cetus). Samples were incubated in a DNA thermocycler (Perkin-Elmer/Cetus) for 35 cycles under the following conditions: 94° C. for 30 s, 55° C. for 30 s, and 72° C. for 30 s. Following amplification, 5 $\mu$l of stop solution (95% formamide, 10 mM NaOH, 0.05% Bromophenol Blue, 0.05% Xylene Cyanol) was added to each sample. Following denaturation for 3 min at 95° C., 5 $\mu$l of each sample was immediately loaded onto prewarmed polyacrylamide gels (6% polyacrylamide, 7M urea) and electrophoresed for 3–4 h. Gels were then placed on Whatman, 3 mm paper and dried in a slab gel dryer. Autoradiographs were created by exposing Kodak Xomat AR film to the dried gels for 24–36 h.

Linkage analysis

Genotypic data from the autoradiographs were entered into a Macintosh computer. A Hypercard-based program (Nichols, B E et al., Am J Hum Genet 51 A369 (1992)) was used to store and retrieve marker data as well as to export it to a DOS-compatible machine for analysis with the computer program LINKAGE (version 5.1) (Lathrop, G M and LaLouel, J M 359, 794–801 (1992)). Allele frequencies were assumed to be equal for each marker. The MLINK routine was used for pairwise analysis. The relative odds of all possible orders of the disease and two markers (D1S191 and D1S194) was performed under the ILINK program. Significance of linkage was evaluated using the standard criterion ($Z_{max}$>3.0).

Results clinical findings

All of the 37 family members studied were at 50% risk of having the disease because of a known affected parent or sibling. Nineteen of these patients had elevated intraocular pressures and visual field defects consistent with the diagnosis of primary open angle glaucoma. Three more patients had moderately elevated intraocular pressures and obviously affected children.

linkage analysis

Over 90 short tandem repeat polymorphisms were typed in the family before linkage was detected with markers that map to the long arm of chromosome 1. Two-point maximum likelihood calculations using all available family members and 33 chromosome 1 markers revealed significant linkage to eight of them (Table 1). D1S212 was fully informative for all affected members of the family, and pairwise linkage analysis produced a lod score of 6.5 ($\theta=0$). Multipoint linkage analysis did not add to the peak lod score. The glaucoma locus was therefore determined to be located in a region of about 20 centiMorgans (cM) in size between D1S191 and D1S194. Both of these markers demonstrated multiple recombinants (two and three, respectively) in affected individuals in the family. The order D1S191-glaucoma-D1S194 was more than 1,000 times more likely than the other two possible orders.

6) Denature samples at 95° C. for 3 minutes and load immediately onto a prewarmed polyacrylamide gel.

7) Dry gels on Whatmann paper and expose autoradiography film for 1–2 days.

Where possible, multiple loadings of different STRPs on gels were performed. Up to 6 markers per gel have been successfully loaded. In addition, the PCR amplification (up to three markers) have been successfully multiplexed. The juvenile glaucoma gene is believed to lie between markers AFM238 and AT3 (an 8 centimorgan interval) based on observed recombinations within the families studied. Haplotypic analysis between families has further narrowed this interval to the 2 centimorgan interval between D1S210 and AT3.

Since the genetic interval has been narrowed significantly physical mapping strategies can be used. The closest flank-

TABLE 1

Pairwise linkage data

| Recombination fraction | 0.05 | 0.10 | 0.15 | 0.20 | 0.25 | 0.30 | 0.40 | $z_{max}$ | $\theta$ | Locus |
|---|---|---|---|---|---|---|---|---|---|---|
| D1S212 | 6.0 | 5.4 | 4.8 | 4.2 | 3.6 | 2.9 | 1.4 | 6.5 | 0.00 | 1 |
| D1S215 | 5.1 | 4.6 | 4.0 | 3.5 | 2.9 | 2.3 | 1.0 | 5.6 | 0.00 | 1 |
| D1S218 | 4.7 | 4.3 | 3.8 | 3.3 | 2.7 | 2.2 | 1.0 | 5.2 | 0.00 | 1 |
| D1S238 | 4.4 | 4.2 | 3.9 | 3.4 | 2.9 | 2.4 | 1.2 | 4.4 | 0.04 | 1 |
| D1S117 | 3.8 | 3.6 | 3.3 | 2.8 | 2.3 | 1.8 | 0.7 | 3.8 | 0.04 | 1q |
| D1S104 | 3.2 | 2.9 | 2.6 | 2.3 | 2.0 | 1.6 | 0.7 | 3.4 | 0.00 | 1q21–q23 |
| D1S191 | 3.0 | 3.2 | 3.0 | 2.7 | 2.4 | 1.9 | 0.9 | 3.2 | 0.09 | 1 |
| D1S196 | 2.9 | 2.6 | 2.3 | 2.0 | 1.6 | 1.3 | 0.5 | 3.1 | 0.00 | 1 |

EXAMPLE 2

Genetic Fine Mapping of the Juvenile Primary Open Angle Glaucoma Locus and Identification and Characterization of a Glaucoma Gene Once primary linkage has been identified, the next step in identifying any disease gene by positional cloning is the narrowing of the candidate locus to the smallest possible genetic region. The initial study described in Example 1 demonstrated that a primary open angle glaucoma gene lies within an approximately 20 cM region flanked by markers D1S194 and D1S191 on chromosome 1q. Additional markers and families were obtained and used to refine the genetic locus to a 2.5 cM region using two of these families. The third family should allow the interval to be further narrowed.

In addition to the family resources, polymorphic DNA markers and genetic maps were used to refine the 1q glaucoma locus. Using STRPs, the genotype of each family member was determined. Amplification of each STRP was performed using the following protocol:

1) Dilute genomic DNA (about 1 $\mu g/\mu l$) 1/50 i.e. 20 $\mu l$ "stock" DNA and 980 dd H$_2$O.
2) Use 2.5 $\mu l$ of "dilute" DNA as template for PCR
3) Prepare PCR reaction mix as follows:
   1.25 $\mu l$ 10 X Buffer (Stratagene)
   0.12 $\mu l$ of each primer (50 pmoles each primer)
   0.5 $\mu l$ dNTPs (5 mM C,T,&G and 0.625 mM A "cold")
   3.5 $\mu l$ dd H$_2$O
   0.25 $\mu l$ $^{35}$S-dATP
   0.1 $\mu l$ Taq polymerase
   oil (one drop)
4) Perform PCR at optimal conditions for given primers (usually 94° 30 s, 55° 30 s and 72° 30 s) and run for 35 cycles.
5) Add 5 $\mu l$ stop solution (95% formamide, 10 mM NaOH, 0.05% bromophenol blue, 0.05% xylene cyanol) to each tube.

ing markers to screen total human genomic yeast artificial chromosome (YAC) libraries to identify YACs mapping to the region of interest. The CEPH and CEPH mega-YAC libraries can be used for this purpose (available from the Centre d'Etude du Polymorphisme Humain (CEPH) Paris, France). Forty-four percent of the clones in the CEPH mega-YAC library have an average size of 560 kb, an additional 21% have an average size of 800 kb, and 35% have an average size of 120 kb. This library is available in a gridded micro-titer plate format such that only 50–200 PCR reactions need to be performed using a specific sequence tagged site (STS) to identify a unique YAC containing the STS. The YAC contigs identified by CEPH have been used to begin constructing a contig across the 1q candidate region (see FIG. 3). YAC contigs using YAC ends can be constructed to identify additional YACs. YAC ends can be rescued using anchored PCR (Riley, J. et al (1990) Nucleic Acids Res 18:2887–2890), the ends can then be sequenced and the sequence can be used to develop a sequence tagged site (STS). The STS can be used to rescreen the YAC library to obtain an overlapping adjacent YAC.

Because some YACs have been shown to be chimeric or to contain deletions or rearrangements, particularly those from the mega YAC library, the correctness of each YAC contig should be verified by constructing a pulse field map of the region. In addition, chimeric YACs are minimized by ensuring that the YAC maps to a single chromosome by fluorescent in situ hybridization (FISH) or that the two YAC ends map to the same chromosome using monochromosomal somatic cell hybrids (NIGMs Panel 2). In addition, the YAC chimera problem can be minimized by not relying on any single YAC to span a given chromosome segment, but rather by obtaining at least two overlapping independent YACs to ensure coverage of a given region.

Once a YAC contig spanning the candidate region has been isolated, this reagent can be used to generate additional genetic markers for potentially finer genetic mapping. In addition, the YACs can be used to make higher resolution physical mapping reagents such as region specific lambda and cosmid clones. Lambda and cosmid clones can be used for isolation of candidate genes. A modification of "exon trapping" (Duyk, G. M. (1990) *Proc Natl Acad Sci USA* 87:8995–8999) known as exon amplification (Buckler, A. J. (1991) *Proc Natl Acad Sci USA* 88:4005–4009) can be used to identify exons from genes within the region. Exons trapped from the candidate region can be used as probes to screen eye cDNA libraries to isolate cDNAs. Where necessary, other strategies can be utilized to identify genes in genomic DNA including screening cDNA libraries with YAC fragments subcloned into cosmids, zoo blot analysis, coincidence cloning strategies such as direct selection of cDNAs with biotin-streptavidin tagged cosmid clones (Morgan, J. G. et al (1992) *Nucleic Acid Res* 20 (19) :5173–5179), and HTF island analysis (Bird, A. P. (1987) *Trends Genet* 3:342–247). Promising genes will be further evaluated by searching for mutations using GC-clamped denaturing gradient gel electrophoresis (Sheffield, V. C. et al (1989) *Genomics* 16:325–332), single strand conformational gel polymorphism (SSCP) analysis (Orita, M. et al (1989) *Proc Natl Acad Sci USA* 86:2766–2770) and direct DNA sequencing.

EXAMPLE 3

Primer Pairs for Use In Identifying Subjects Having a Predisposition to Glaucoma Two primer pairs that can be used in conjunction with the polymerase chain reaction to amplify a 190 base pair sequence from human genomic DNA that harbors mutations causing glaucoma (primers 1 and 2 in Table 1) have been identified.

TABLE 1

| Primer 1 | forward - ATACTGCCTAGGCCACTGGA (SEQ ID NO. 1) |
| | reverse - CAATGTCCGTGTAGCCACC (SEQ ID NO. 2) |
| Primer 2 | forward - GAACTCGAACAAACCTGGGA (SEQ ID NO. 3) |
| | reverse - CATGCTGCTGTACTTATAGCGG (SEQ ID NO. 4) |

These primers which hybridize to a portion of the Trabecular Meshwork Induced Glucocorticoid (TIGR) gene (International Publication No. 96/14411 to Nguyen et al.) were used to screen 410 patients with glaucoma and 81 normal individuals. Four amino acid altering sequence changes were detected in a total of 12 glaucoma patients (2.9%). No amino acid altering sequence changes were observed in the normal individuals.

The specific mutations observed are shown in FIG. 4 below the normal sequence. The prevalence of mutations in the segment of DNA amplified by these primer pairs suggest that use of these primers in conjunction with an appropriate detection method can be used to identify a predisposition to glaucoma in approximately 100 thousand patients in the United States alone.

Equivalents

Those skilled in the art will recognize, or be able to ascertain using no more than routine experimentation, many equivalents of the specific embodiments of the invention described herein. Such equivalents are intended to be encompassed by the following claims.

We claim:

1. An isolated nucleic acid molecule consisting of a member selected from the group consisting of SEQ ID NO: 1, SEQ ID NO: 2, SEQ ID NO: 3, SEQ ID NO: 4, and complements thereof.

2. An isolated nucleic acid molecule consisting of SEQ ID NO: 6 or the complement thereof.

3. A kit for diagnosing a subject as having primary open angle glaucoma comprising:

a) a primer pair selected from the group consisting of SEQ ID NOS: 1 and 2, and SEQ ID NOS: 3 and 4; and b) instructions for using said primer pairs in performing a PCR amplification.

4. A nucleic acid molecule of claim 1, which is SEQ ID NO: 1 or the complement of SEQ ID NO: 1.

5. A nucleic acid molecule of claim 1, which is SEQ ID NO: 2 or the complement of SEQ ID NO: 2.

6. A nucleic acid molecule of claim 1, which is SEQ ID NO: 3 or the complement of SEQ ID NO: 3.

7. A nucleic acid molecule of claim 1, which is SEQ ID NO: 4 or the complement of SEQ ID NO: 4.

8. A primer pair consisting of SEQ ID NOS: 1 and 2.

9. A primer pair consisting of SEQ ID NOS: 3 and 4.

10. An isolated nucleic acid molecule consisting of SEQ ID NO: 7 or the complement thereof.

* * * * *